United States Patent [19]

Sinai-Zingde

[11] Patent Number: 5,300,690

[45] Date of Patent: Apr. 5, 1994

[54] POLYOXIME DERIVED FROM CARBON MONOXIDE-PROPYLENE POLYKETONE

[75] Inventor: Gurudas D. Sinai-Zingde, Mohegan Lake, N.Y.

[73] Assignee: Akzo N.V., Arnhem, Netherlands

[21] Appl. No.: 961,005

[22] Filed: Oct. 14, 1992

[51] Int. Cl.$^5$ .................... C07C 251/32; C08G 85/02
[52] U.S. Cl. ................................... 564/268; 528/228; 528/229; 564/259
[58] Field of Search ................ 564/259, 268; 528/228, 528/229

[56] References Cited

U.S. PATENT DOCUMENTS 5,109,047  4/1992  Aaronson et al. ................. 524/357

FOREIGN PATENT DOCUMENTS 0372602  6/1990  European Pat. Off. .

OTHER PUBLICATIONS

S. J. Kim et al., "Preparation of a Novel Polyoxime and Reversible Uptakes of Molecular Oxygen and Carbon Monoxide by its Metal Complexes", Die Makromolekulare Chemie 175, 125–136 (1974).
M. M. Brubaker et al., "Synthesis and Characterization of Ethylene/Carbon Monoxide Copolymers, etc." *J. Am. Chem. Soc.*, vol. 74, 1509–1515 (1952).

*Primary Examiner*—Richard L. Raymond
*Assistant Examiner*—P. O'Sullivan
*Attorney, Agent, or Firm*—Richard P. Fennelly; Louis A. Morris

[57] ABSTRACT

A polyoxime can be formed by reacting hydroxylamine with a copolymer of carbon monoxide and propylene. When the relative amount of oxime units in the polyoxime is high the polyoxime is soluble in water. Conversely, solubility in organic solvent is conferred when the oxime content is relatively low.

3 Claims, No Drawings

POLYOXIME DERIVED FROM CARBON MONOXIDE-PROPYLENE POLYKETONE

BACKGROUND OF THE INVENTION

In certain early publications dealing with polyketone compositions, it was suggested that polyoximes can be formed by the reaction of a polyketone with hydroxylamine. For example, M. M. Brubaker et al. in J. of the Amer. Chem. Soc., Vol. 74, pp. 1509-1515, describes certain free radical initiated-polyketone compositions formed by polymerizing carbon monoxide and ethylene which could be formed into polyoximes by reaction with hydroxylamine. These polyketone compositions are quite dissimilar from the linear, alternating polyketones more recently developed, and the Brubaker et al. publication merely covers the possibility of copolymerizing ethylene with carbon monoxide. The polyoxime that was formed by Brubaker had 78% of its carbonyl groups converted to oxime groups. This polyoxime was insoluble in water.

A more recent publication by S. J. Kim et al. in Die Makromolekulare Chemie, 175, 125-136 (1974), also describes polyketones of carbon monoxide and ethylene Which are indicated as being synthesized by a method similar to that used by Brubaker et al. In this publication the polyoximes are said to be soluble only in mixtures of organic solvents such as ethanol/dioxane or ethanol/acetone. They are indicated as also dissolving both in mineral acid and base, such as more than 10% aqueous sulfuric acid, aqueous sodium carbonate, sodium hydroxide, and the like.

More recently, in European Patent Publication No. 372,602, certain thermoset resins are described which are obtained by curing a thermoplastic polymer which can be obtained by reacting a curing agent with a linear, alternating copolymer of carbon monoxide and one or more olefinically unsaturated compounds. Although this patent lists propene as one possible monomer that can be used in forming the polyketone compositions that it teaches can be converted to other structures, no actual examples of conversion of a carbon monoxide-propylene polyketone to a polyoxime are actually shown in this patent.

SUMMARY OF THE PRESENT INVENTION

The present invention relates to a novel polyoxime obtained by reacting hydroxylamine with a copolymer of carbon monoxide and propylene. This polyoxime, depending upon the amount of hydroxylamine used converted to the polyoxime, can either be made soluble or insoluble in water or in organic solvent.

DETAILED DESCRIPTION OF THE PRESENT INVENTION

The starting material for ultimate conversion to the polyoxime of the present invention is a carbon monoxide-propylene polyketone which can be synthesized by utilizing a catalyst composition based on a palladium compound, an acid having a $pK_a$ of less than 6, and a bidentate compound of arsenic, antimony, phosphorus or nitrogen of the type mentioned in European Patent Publication No. 301,664. The solvent that is used for the synthesis of the carbon monoxide-propylene copolymer is preferably one which is essentially ketonic in nature. Representative ketones which can be used include the $C_1$–$C_4$ ketones such as acetone, diethyl ketone, ethylpropyl ketone, dipropyl ketone, and methyl isobutyl ketone. Acetone is a preferred type of solvent to use. The polyketone that is formed in such a solvent medium is essentially free of ester- and ether-termination structures. Details regarding this type of copolymer are given in published International Patent Application No. WO 92/07019, published Apr. 30, 1992. U.S. Pat. No. 5,109,047 relates to the use of this type of copolymer as a plasticizer for vinyl chloride polymers.

In order to form the type of polyoxime compositions contemplated by the present invention, the foregoing type of carbon monoxide-propylene polyketone is treated with the desired amount of hydroxylamine in a suitable solvent such as a mixture of isopropanol and water. The polyoxime that is formed will comprise the recurring unit:

—[H$_2$C—CH(CH$_3$)—C(=NOH)]— and if the amount of polyoxime is sufficiently large, e.g., above about 50% by weight, the resulting polyoxime will be soluble in aqueous solution. The presence of lesser amounts of oxime units will render it water insoluble. Conversely, having a rather low oxime content, below about 30%, will render the polyoxime compositions of the present invention soluble in organic solvent, whereas higher oxime contents render them increasingly more insoluble. The polyoximes of the present invention have been found to be soluble, in general, in alcohols such as ethanol.

The polyoxime compositions of the present invention are deemed to be useful as antioxidants and chelating agents.

The present invention is further illustrated by the Examples which follow.

EXAMPLES 1-20

A copolymer of carbon monoxide and propylene having a molecular weight of about 4000 gm/mole was reacted with varying amounts of hydroxylamine (H$_2$NOH) in an isopropanol/water solvent medium at a temperature of about 55° C. to form a variety of oxime derivatives of the copolymer. More specifically, in order to form a product using 1.0 mole equivalent of hydroxylamine, 85.9 gm of such a copolymer were dissolved in 250 mL of 2-propanol by warming the mixture of copolymer and alcohol to 656° C. Then, a hydroxylamine solution was separately obtained by neutralizing a solution of 119.4 gm of hydroxylamine hydrochloride in 215 mL of water with 68.7 gm of sodium hydroxide in 86 mL of water. This hydroxylamine solution was then slowly added to the previously described copolymer solution which was maintained at 55° C. After two hours, the resulting mixture of solutions was then poured onto 250 gm of crushed ice and was filtered. The tacky mass thus obtained was washed with small amounts of ice-cold water and was dried in a vacuum oven to obtain 95 gm of a powdery material which was the desired polyoxime product. The presence of the oxime group was confirmed in this product by spectroscopic analysis.

Similar procedures were employed to prepare 0.2 and 0.5 mole equivalent oximes utilizing the appropriate amounts of hydroxylamine in each case.

Each of the products was then tested for their solubility in a variety of solvents as set forth in the Table which follows

| ("+" indicates that the product was soluble; "−" indicated insolubility): | | | | | |
|---|---|---|---|---|---|
| $H_2NOH$ (Mole Eq.) | Water | Ethanol | Butyl Acetate | Methyl Ethyl Ketone | Toluene |
| 0 | − | + | + | + | + |
| 0.2 | − | + | + | + | + |
| 0.5 | + | + | − | − | − |
| 1.0 | + | + | − | − | − |

The data presented above demonstrates that as the amount of hydroxylamine is increased, the resulting oxime-modified polymer exhibits a greater degree of solubility in water and a lesser degree of solubility in organic solvent.

The foregoing Examples, since they are intended to merely illustrate certain embodiments of the present invention, should not be construed in a limiting sense. The scope of protection sought is set forth in the claims which follow.

I claim:

1. A polyoxime, obtained by reacting hydroxylamine with a linear, alternating copolymer of carbon monoxide and propylene, which comprises the recurring unit: $-[H_2C-CH(CH_3)-C(=NOH)]-$.

2. A polyoxime as claimed in claim 1 which is soluble in organic solvent and insoluble in water.

3. A polyoxime as claimed in claim 1 which is insoluble in organic solvent and soluble in water.

* * * * *